United States Patent [19]

Guillou et al.

[11] Patent Number: Plant 7,273

[45] Date of Patent: Jul. 17, 1990

[54] VARIETY OF GERANIUM NAMED GIGI

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 360,013

[22] Filed: Jun. 1, 1989

[30] Foreign Application Priority Data

Apr. 11, 1989 [FR] France ..... 8530

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenheim & Webb

[57] ABSTRACT

A new geranium having a plant habit which is fuller, resulting in higher cutting production. The plant form is much more compact than the current market varieties which produces the fuller plant. The single salmon-coral florets accent the medium green foliage. This variety has been garden tested and found to be much more heat tolerant and self-cleaning than those ivies currently sold.

1 Drawing Sheet

BACKGROUND OF THE NEW PLANT

The present invention comprises a new and distinct cultivar of *Pelargonium* × *peltalum* known by the varietal name Gigi (Oglevee Ltd. U.S. Plant Pat. No. 7,036, French No. 555 Guisully). The new variety was discovered in a selective breeding program by Messrs. Jacques, Maurice and Bernard Guillou. The new variety is a selection from a crossing of Cocorico × No. 90. The new variety has a more orange color flower than its parentage.

The new cultivar was discovered in 1986 at 55 rue Godard, 35400 Saint-Malo, France, was first asexually reproduced by cuttings during 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., using full light, 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Feb. 17, 1989 and flowered on Apr. 18, 1989 and the color readings were taken shortly thereafter. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium* × *peltatum.*

*Commercial.*—Ivy Geranium (U.S. Plant Pat. No. 7,036) Gigi.

Form: Cascading mound habit.

Height: 19–21 cm from media surface.

Growth: Free branching, upright growth with cascading side growth.

Strength: Has an upright mound habit while outer branches cascade over the pot.

Foliage: Stalked leaf attachment; no zone present.

Leaves:

*Size.*—7.5–8.5 cm; fully expanded leaf.

*Shape.*—Reniform, cordate base.

*Margin.*—Pedately lobed.

*Texture.*—Smooth; reflective.

*Color.*—Green Group 137C.

*Ribs and veins.*—Yellow-Green Group 146B.

Petioles: 5–7.5 cm in length.

*Color.*—Yellow-Green Group 146B.

Stem:

*Color.*—Yellow-Green Group 146B.

*Internodes.*—2–5 cm in length.

THE BUD

Shape: Elliptical cluster; peduncle is bent allowing umbel to droop until maturity when the umbel and peduncle stand straight.

Size: 2–3 cm across.

INFLORESCENCE

Blooming habit: Continuous; upright; single floret.

Size: 9–10 cm across.

Borne: Florets on pedicel; pedicel on peduncle; umbel 3–5 cm above foliage canopy.

Florets:

*Form.*—Flat to slightly cupped.

*Color.*—Top: Red Group 47C; Venation of two upper petals: Red-Purple Group 60B. Bottom: Red Group 43C.

*Petals.*—5 in number, separate, not united; margin entire.

*Floret size.*—5–6 cm across.

*Texture and appearance.*—Smooth; single florets containing 5 petals; appearance from a distance is a rich salmon-coral with burgundy markings on upper petals.

Petaloids:

*Quantity.*—None present.

Pedicel: 3.5–4 cm in length.

*Color.*—Greyed-Purple Group 183B.

Peduncle: 15–17 cm in length.

*Color.*—Yellow-Green Group 146B.

Disease resistance: None known.

Lasting quality: The single bloom and foliage tend to hold up longer in high outdoor temperatures.

REPRODUCTIVE ORGANS

Stamens:

*Anthers.*—3 mm in length.

*Filaments.*—10–11 mm in length; white at base, pink at tip.

*Pollen.*—Golden brown.

Pistils:

*Number.*—One.

*Length.*—12–15 mm.

*Stigma.*—5 or 6 parted.

*Style.*—6–7 mm in length; white.

Ovaries: Superior; pubescent; pale green; 6–7 mm in length, 2–3 mm in width.

Fruit: None observed.

GENERAL CHARACTERISTICS

Gigi has many new and outstanding features for an ivy geranium. The plant habit is fuller, resulting in higher cutting production. The plant form is much more compact than the current market varieties which produces a fuller plant. The single salmon-coral florets accent the medium green foliage. This variety has been garden tested and found to be much more heat tolerant and self-cleaning than those ivies currently sold.

When compared to the variety "King of Balcon", Gigi has larger petals, larger flowers, more heat tolerance, larger ivy leaf and less trailing habit.

We claim:

1. A new and distinct variety of ivy geranium plant as shown and described herein, and characterized by a full plant habit resulting in higher cutting production, a more compact plant form than the current market varieties, a fuller plant, the single salmon-coral florets accent the medium green foliage and much more heat tolerant and self-cleaning than those ivies currently sold.

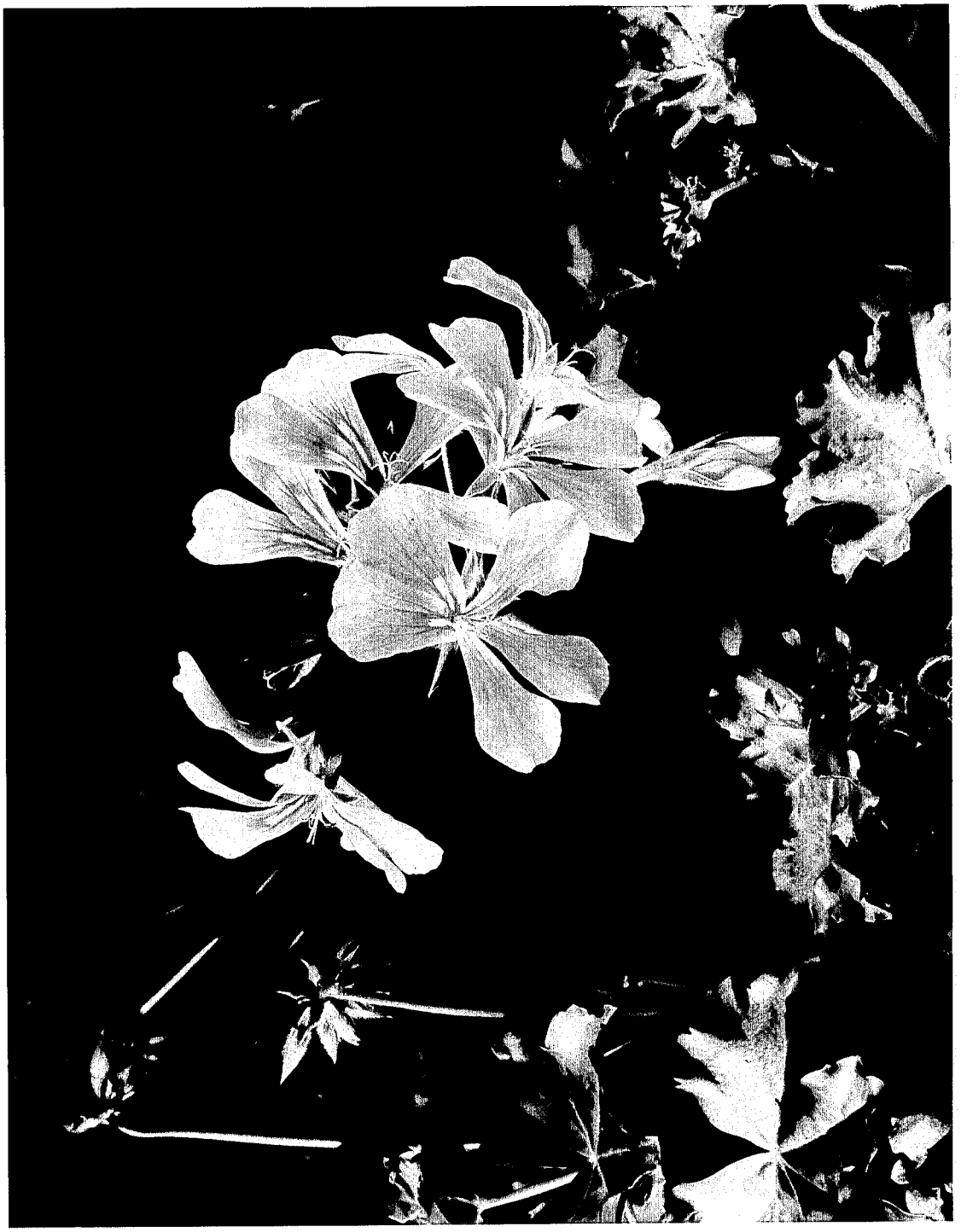

* * * * *